(12) United States Patent
Chen et al.

(10) Patent No.: US 10,468,270 B2
(45) Date of Patent: Nov. 5, 2019

(54) PERFORMING PLANARIZATION PROCESS CONTROLS IN SEMICONDUCTOR FABRICATION

(71) Applicant: Taiwan Semiconductor Manufacturing Co., Ltd., Hsinchu (TW)

(72) Inventors: Chunhung Chen, Hsinchu (TW); Sheng-Chen Wang, Taichung (TW); Chin Wei Chuang, Taichung (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 0 days.

(21) Appl. No.: 15/879,490

(22) Filed: Jan. 25, 2018

(65) Prior Publication Data

US 2019/0164777 A1 May 30, 2019

Related U.S. Application Data

(60) Provisional application No. 62/592,587, filed on Nov. 30, 2017.

(51) Int. Cl.
| | |
|---|---|
| *H01L 21/321* | (2006.01) |
| *G01N 23/20* | (2018.01) |
| *H01L 21/66* | (2006.01) |
| *G06F 11/07* | (2006.01) |
| *G01N 1/10* | (2006.01) |
| *B24B 37/013* | (2012.01) |

(52) U.S. Cl.
CPC ..... *H01L 21/3212* (2013.01); *G01N 23/20075* (2013.01); *G06F 11/07* (2013.01); *H01L 22/26* (2013.01); *B24B 37/013* (2013.01); *G01N 1/10* (2013.01)

(58) Field of Classification Search
USPC .......................................................... 451/5
See application file for complete search history.

(56) References Cited

U.S. PATENT DOCUMENTS

| | | | | |
|---|---|---|---|---|
| 6,629,879 | B1 * | 10/2003 | Kim | G01N 23/223 257/E21.304 |
| 8,716,841 | B1 | 5/2014 | Chang et al. | |
| 8,736,084 | B2 | 5/2014 | Cheng et al. | |
| 8,837,810 | B2 | 9/2014 | Chen et al. | |
| 2005/0050946 | A1 * | 3/2005 | Nishioka | B08B 13/00 73/104 |
| 2006/0072701 | A1 * | 4/2006 | van Kessel | G01N 23/06 378/47 |

(Continued)

FOREIGN PATENT DOCUMENTS

| | | | |
|---|---|---|---|
| WO | WO 2009/139912 A2 | 11/2009 | |
| WO | WO 2011/094568 A2 | 8/2011 | |

*Primary Examiner* — Roberts P Culbert

(74) *Attorney, Agent, or Firm* — Haynes and Boone, LLP

(57) ABSTRACT

A planarization process is performed to a wafer. In various embodiments, the planarization process may include a chemical mechanical polishing (CMP) process. A byproduct generated by the planarization process is collected and analyzed. Based on the analysis, one or more process controls are performed for the planarization process. In some embodiments, the process controls include but are not limited to process endpoint detection or halting the planarization process based on detecting an error associated with the planarization process.

20 Claims, 16 Drawing Sheets

(56) References Cited

U.S. PATENT DOCUMENTS

| | | |
|---|---|---|
| 2008/0031510 A1* | 2/2008 | Jung .................... B24B 37/042 |
| | | 382/149 |
| 2012/0308112 A1 | 12/2012 | Hu et al. |
| 2013/0201461 A1 | 8/2013 | Huang et al. |
| 2013/0258304 A1 | 10/2013 | Chang et al. |
| 2014/0101624 A1 | 4/2014 | Wu et al. |
| 2014/0111779 A1 | 4/2014 | Chen et al. |
| 2014/0119638 A1 | 5/2014 | Chang et al. |
| 2014/0123084 A1 | 5/2014 | Tang et al. |
| 2014/0226893 A1 | 8/2014 | Lo et al. |
| 2014/0253901 A1 | 9/2014 | Zhou et al. |
| 2014/0256067 A1 | 9/2014 | Cheng et al. |
| 2014/0257761 A1 | 9/2014 | Zhou et al. |

\* cited by examiner

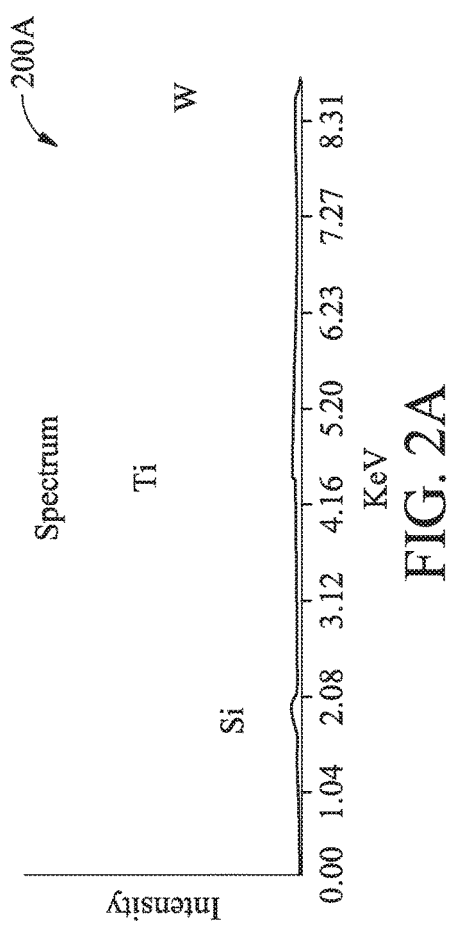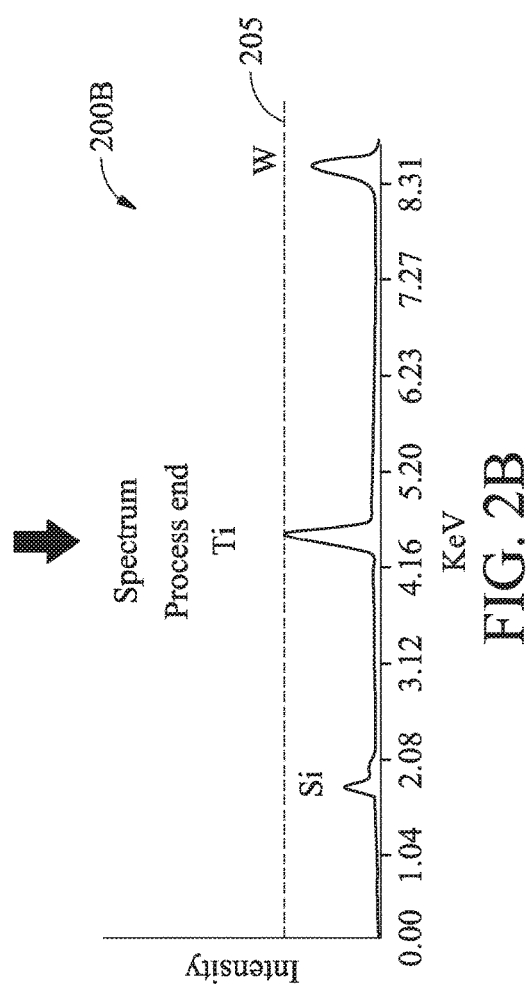
FIG. 2A
FIG. 2B

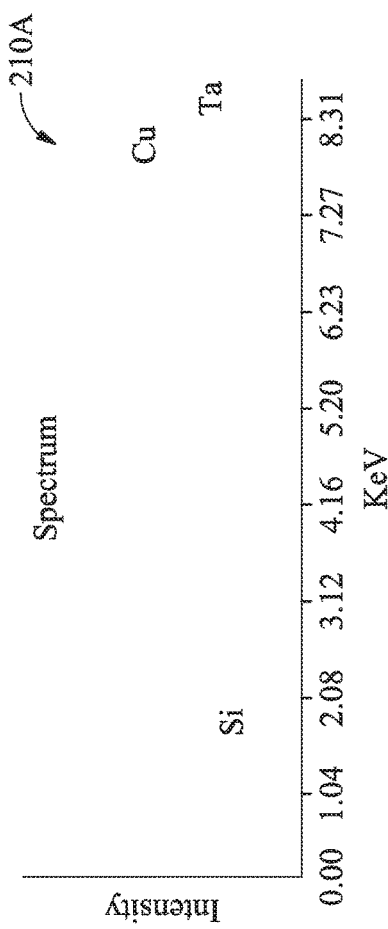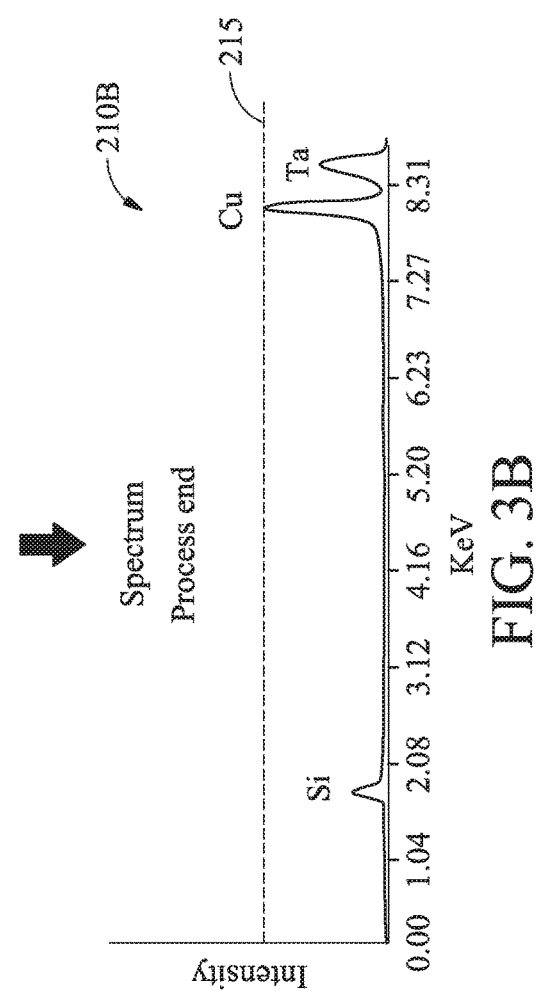

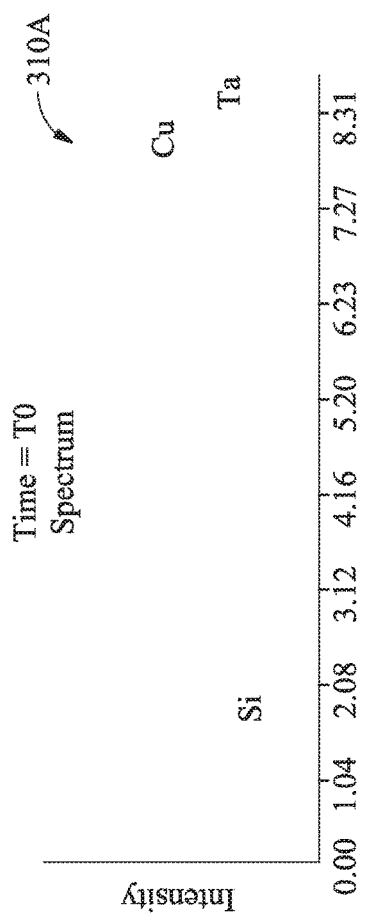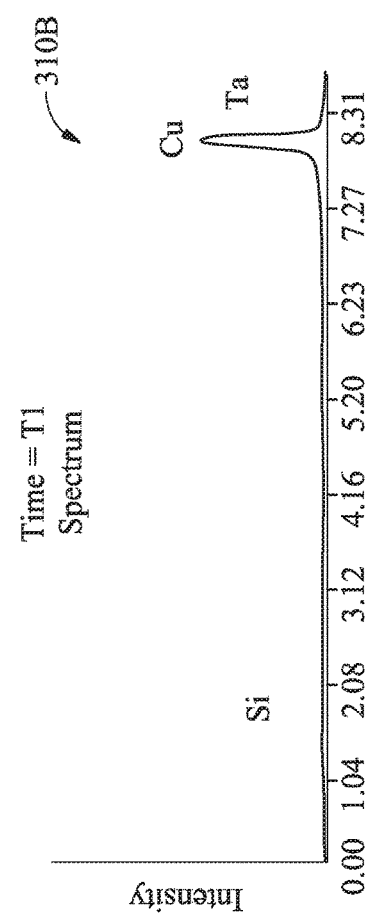

PERFORMING PLANARIZATION PROCESS CONTROLS IN SEMICONDUCTOR FABRICATION

PRIORITY DATA

This application claims priority from U.S. Provisional Patent Application No. 62/592,587, entitled "Performing Planarization Process Controls based on Captured Byproduct Samples" and filed on Nov. 30, 2017, the disclosure of which is incorporated herein in its entirety.

BACKGROUND

The semiconductor integrated circuit (IC) industry has experienced rapid growth. Technological advances in IC materials and design have produced generations of ICs where each generation has smaller and more complex circuits than the previous generation. However, these advances have increased the complexity of processing and manufacturing ICs and, for these advances to be realized, similar developments in IC processing and manufacturing are needed. In the course of integrated circuit evolution, functional density (i.e., the number of interconnected devices per chip area) has generally increased while geometry size (i.e., the smallest component (or line) that can be created using a fabrication process) has decreased.

Planarization processes such as chemical mechanical polishing (CMP) processes are performed as a part of semiconductor fabrication. For example, a CMP process may apply a slurry to a surface of a wafer that needs to be planarized. The slurry has corrosive properties and chemically etches the wafer. In conjunction with the application of the slurry, a polishing pad having a smooth surface is pressed against the surface of the wafer to grind the wafer surface. As a result, the wafer surface becomes substantially flattened (or planarized) to facilitate subsequent fabrication. Existing CMP methods have utilized various process control methods to ensure that the CMP process achieves the desired result. However, conventional CMP process control methods have not analyzed byproduct components generated during a CMP process, or use the byproduct component analysis for purposes of CMP process control.

Therefore, although existing methods and systems of performing planarization processes such as CMP have been generally adequate for their intended purposes, they have not been entirely satisfactory in every aspect.

BRIEF DESCRIPTION OF THE DRAWINGS

The present disclosure is best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

FIGS. 2A-2B, 3A-3B, 4A-4D, 5A-5D, 6A-6B, 7A-7B, and 8A-8B illustrate energy spectrum graphs according to various embodiments of the present disclosure.

DETAILED DESCRIPTION

Figure 1:
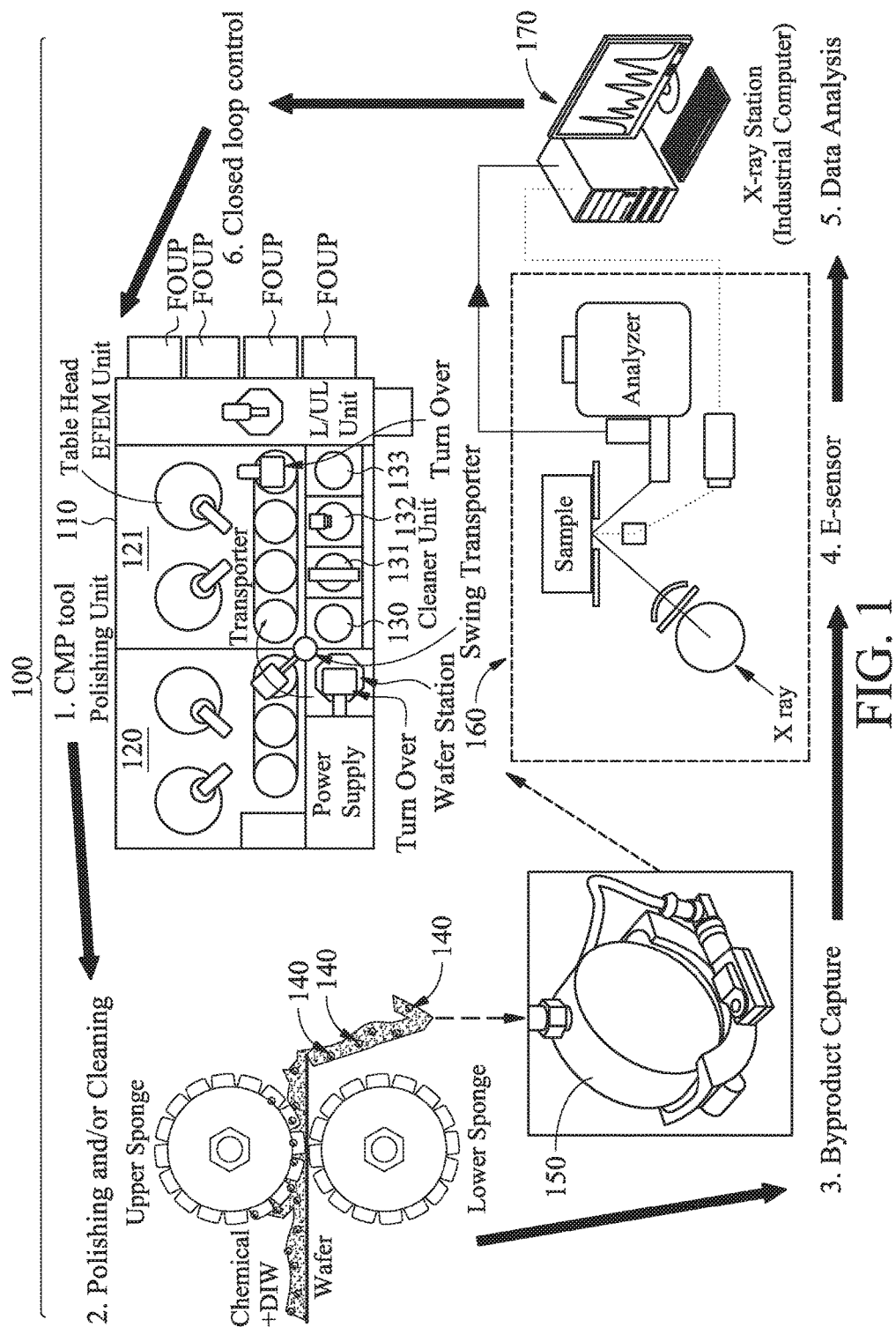
FIG. 1 illustrates a system for performing planarization process control according to embodiments of the present disclosure.

It is understood that the following disclosure provides many different embodiments, or examples, for implementing different features of the invention. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the sake of simplicity and clarity and does not in itself dictate a relationship between the various embodiments and/or configurations discussed. Moreover, various features may be arbitrarily drawn in different scales for the sake of simplicity and clarity.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. For example, if the device in the figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

Semiconductor fabrication may involve performing planarization processes to planarize or flatten a wafer surface, so as to facilitate the ensuing fabrication steps. Chemical mechanical polishing (CMP) is an example planarization process. In a typical CMP process, a chemical slurry application works in conjunction with a mechanical grinding by a polishing pad against a wafer surface to flatten the wafer surface topography. CMP control methods may involve parameters such as time (e.g., polishing time), rate (e.g., etching rate of the slurry or polishing rate), optical measurements, etc. However, these control methods may not provide sufficiently accurate feedback as to how well the CMP process is being performed, or when it should be stopped. In addition, conventional CMP process control methods cannot accurately predict process abnormality. As such, conventional CMP process controls are inadequate.

According to the various aspects of the present disclosure, CMP process byproducts are collected. CMP process products may include the materials (e.g., liquid containing chemicals or debris) generated as a result of the CMP etching/polishing processes or cleaning processes. The collected CMP byproducts are then analyzed, for example with respect to the presence of certain elements, the weighting of the elements, and/or a chronological sequence in which a plurality of elements appear. The analysis results may be used to optimize CMP process control, as discussed in more detail below.

FIG. 1 illustrates simplified representations of various components of a system 100 of performing CMP process control according to various aspects of the present disclosure. The system 100 is broken down into a plurality of stages 1-6, and thus FIG. 1 also illustrates a CMP control process flow using the system 100.

At stage 1, the CMP process control system 100 uses a CMP tool 110 to polishing and clean one or more wafers. The CMP tool 110 includes an equipment front end module (EFEM) unit. The EFEM unit may include a plurality of front opening unified pods (FOUP) and a load/unload (L/UL) unit. The EFEM unit loads wafers into the CMP tool 110 and unloads the wafers out from the CMP tool 110.

The CMP tool 110 also includes a polishing unit. The polishing unit may include one or more polishing chambers, for example polishing chambers 120-121. Each of the polishing chambers 120/121 may include tools such as polishing tables, polishing heads, platens, slurry delivery systems, pad conditioners, etc., for polishing one or more wafers. In some embodiments, multiple wafers may be polished simultaneously. The polishing chambers 120 may also include transporters or swing transporters for transporting the wafers to and from the polishing chambers, as well as turn over wafer stations (or just turn over tools) for turning over (or flipping) the wafer (so as to polish an opposite side of the wafer). Thus, the polishing target of the polishing chambers 120-121 may also include a front side of wafers, a back side of wafers, as well as wafer edges. In various embodiments, the wafers may be a patterned wafer or a non-patterned wafer, may contain a semiconductor material (e.g., Si or SiGe), an epitaxially grown material, a conductive material (e.g., metal), a glass material, and/or a dielectric material. The polishing processes performed by the polishing chambers 120-121 may be utilized in semiconductor fabrication (e.g., planar semiconductor devices or FinFET devices), light-emitting diode (LED) manufacture, liquid crystal display (LCD) manufacture, solar device manufacture, and/or wafer packaging processes such as wafer bumping, as non-limiting examples.

The CMP tool 110 also includes a cleaner unit (also referred to as a cleaning unit). The cleaner unit may include a plurality of cleaning chambers, for example cleaning chambers 130, 131, 132, and 133. Each of the cleaning chambers 130-133 may include tools for cleaning and/or rinsing the wafers, for example after the wafers have been partially or completely polished. The cleaning chambers 130-133 may apply a liquid such as de-ionized water (DIW) to the polished wafer surface to wash away debris or other byproducts generated as a part of the wafer polishing. In some embodiments, additional chemicals may be added to the DIW to facilitate the rinsing or cleaning of the wafer. Some of the cleaning chambers (such as the cleaning chamber 131) may also include one or more sponges that may be used to scrub the wafer surface, so as to facilitate the removal of the debris/byproduct without damaging the wafer surface. After the wafers are cleaned by the cleaning chambers 130-133, they may still be transported back to the polishing chambers 120-121 for further polishing, depending on control instructions received from a controller.

Stages 2 and 3 of the CMP process control system 100 illustrate the collection or capture of the byproducts of the CMP process. As a non-limiting example, stage 2 in FIG. 1 illustrates CMP byproducts (e.g., byproducts 140) being generated during a cleaning process. Using a cleaning chamber such as the cleaning chamber 131 of the CMP tool 110, a liquid that contains DIW and a cleaning chemical may be applied to a wafer, and an upper sponge may be used to scrub an upper surface of the wafer, and a lower sponge may be used to scrub a lower surface of the wafer. Byproducts such as byproducts 140 may be generated. The byproducts may include debris (such as polished-off portions of the wafer) from the wafer as a result of the polishing or cleaning. In some embodiments, the byproducts 140 may contain elements of the wafer such as semiconductor materials, metal materials, dielectric materials, and/or the materials corresponding to the etching slurry or cleaning solutions.

The byproducts 140 may be collected/captured by a byproduct capture tool 150 in stage 3 of the CMP process control system 100. For example, the byproduct capture tool 150 may include a container that is connected (e.g., via hoses or ducts) to the cleaning unit or the polishing unit of the CMP tool 110. In some embodiments, the byproduct capture tool 150 includes a liquid analyzer tool. In some embodiments, the byproduct capture tool 150 is configured to be substantially free of contaminant particles. This is so that the byproduct capture tool 150 itself will not contribute elements that are not in the collected byproducts 140, which could confound the byproduct analysis in subsequent stages.

Although FIG. 1 illustrates the collecting/capturing the byproducts 140 during wafer cleaning, it is understood that the byproducts may be collected/captured during wafer polishing as well. In other words, the byproduct capture tool 150 may be collecting/capturing the byproducts from the polishing chambers 120-121, instead of, or in addition to, from the cleaning chambers 130-133.

At a stage 4 of the CMP process control system 100, an e-sensor device 160 may be used to detect and/or analyze the CMP byproducts collected/captured by the byproduct capture tool 150. In some embodiments, the e-sensor device 160 includes a capture component, an analyzer component, and a computer component. In some embodiments, the e-sensor device 160 includes an X-ray device, which may apply X-rays to the samples of the captured CMP byproducts. In other embodiments, the e-sensor device 160 may shoot other rays/waves to the captured CMP byproducts, such as Energy Dispersive X-ray Fluorescence (EDXRF), Wavelength Dispersive X-ray Fluorescence (WDXRF), Total Reflection X-ray Fluorescence (TXRF), ultraviolet (UV), infrared (IR), light scattering, and/or ultrasonic wave, in order to detect and/or analyze the CMP byproducts. By bombarding these rays/waves against the collected CMP byproducts, the presence and the intensity/weighting of various elements in the CMP byproducts may be revealed, which can then be used to determine CMP process control, as discussed below in more detail.

Still referring to FIG. 1, the e-sensor device 160 may also include a chain of multi-sensors in some embodiments. For example, multiple e-sensor devices may be used to detect and analyze the CMP products from multiple wafers and/or from multiple stages (e.g., from the polishing unit and from the cleaning unit). This will allow the process to be performed in less time, which may facilitate real-time monitoring and process control of CMP. In some embodiments, the e-sensor device 160 includes a XRF Analyzer tool. In some embodiments, the byproduct capture tool 150 and the e-sensor device 160 may be integrated into a single tool. Alternatively stated, a single tool may be used to perform both the capturing of the CMP byproducts and the detection and analysis of the CMP byproducts. In other embodiments, multiple standalone byproduct capture tools 150 may be deployed to collect the CMP byproducts for the multiple e-sensor devices to analyze the collected CMP byproducts, respectively.

At stage 5 of the CMP process control system 100, data analysis may be performed. The data analysis may be performed using an industrial-grade computer 170, which may have much greater data processing capabilities than personal desktop or laptop computers. Therefore, a large volume of complex data (e.g., "big data")—which may be collected from numerous wafers at numerous different phases of polishing/cleaning—may be analyzed in stage 5. In some embodiments, the industrial grade computer 170 may include an X-ray station.

The data analysis results from stage 5 are then fed back to the CMP tool 110 in stage 6 as part of a closed loop control. For example, if the data analysis results from stage 5 indicate a process abnormality due to detecting a presence of an unknown element in the CMP byproduct, the CMP tool 110 may be instructed to stop polishing according to the closed loop control. As another example, if the data analysis results from stage 5 indicate that the CMP process has reached its intended stopping point (e.g., end-point detection), the CMP tool 110 may be instructed by the closed loop control of stage 6 to finish the CMP process, since the CMP process has been satisfactorily performed. In some embodiments, the closed loop control and the CMP processes may be performed substantially in real-time.

Various examples of using the CMP byproduct analysis to perform CMP process control will now be discussed.

FIGS. 2A and 2B illustrate example energy spectrum graphs 200A and 200B associated with a tungsten (W) CMP process. The graph 200A corresponds to a first point in time, for example at or near a beginning of the CMP process. The graph 200B corresponds to a second point in time, for example at or near an end of the CMP process. In both graphs 200A and 200B, an X-axis represents an energy spectrum (with a unit of kilo-electron-volts, or KeV), and a Y-axis represents an intensity (with a unit of cps).

As discussed above, the analysis of the CMP byproducts may involve bombarding the collected CMP byproduct samples with a ray or a wave, such as X-ray, EDXRF, WDXRF, TXRF, UV, IR, light scattering, or ultrasonic wave. In response to the ray or wave bombarding the collected CMP byproduct samples, different energy bands that correspond to different elements may manifest different intensities. For example, as shown in FIG. 2B, the element silicon (Si) may have a corresponding energy band of between about 1.5 KeV and about 2.1 KeV, the element titanium (Ti) may have a corresponding energy band of between about 4.1 KeV and about 4.7 KeV, the element tungsten (W) may have a corresponding energy band of between about 8.2 KeV and about 8.5 KeV. Of course, it is understood that the numbers for these ranges are merely examples and are not intended to be limiting. Meanwhile, the intensity of these elements (e.g., the peaks in the Y-axis corresponding to the elements) may be correlated with an amount of the element in the captured CMP byproduct sample. As the amount of the element in the captured CMP byproduct sample increases, so does the intensity of that element's peak in the Y-axis, and vice versa. The e-sensor device 160 discussed above can detect or measure the energy spectrum versus intensity for the different elements.

The tungsten CMP process associated with FIGS. 2A-2B may be performed to planarize a wafer surface after a tungsten plug (e.g., a conductive contact) has been deposited into an opening. As shown in FIG. 2A, the elements Si, Ti, and W have low intensities, which means that the presence of the elements Si, Ti, and W is low in the captured CMP byproduct samples. This is expected, since FIG. 2A corresponds to a point in time at or near a beginning of the CMP process, where not much of the wafer has been polished off yet.

As shown in FIG. 2B, the elements Si, Ti, and W have high intensities, to the point where they are clearly observable on the graph 200B. This means that the presence of the elements Si, Ti, and W is high in the captured CMP byproduct samples. The presence of high amounts of Si, Ti, and W is expected, since FIG. 2B corresponds to a point in time at or near an end of the CMP process, where a sufficient amount of the wafer has been polished off. In some embodiments, the intensity of any given element has to meet an intensity threshold before the element can be considered to have a sufficient amount of presence in the CMP byproduct. For example, a peak of the element Ti has to meet an intensity threshold 205. The peaks of the elements Si and W have to meet other respective intensity thresholds, which are not specifically illustrated herein for reasons of simplicity and may have different values than the intensity threshold 205. These intensity thresholds may be determined before the CMP process is performed. In some embodiments, each of the intensity thresholds may be set by engineers, for example as a function of the baseline intensity of the respective element. According to the various aspects of the present disclosure, when the peaks of the elements Si, Ti, and W meet their respective intensity thresholds, the CMP process may be considered to have been satisfactorily performed and thus may stop. In this manner, the present disclosure uses analysis of captured CMP byproducts to determine the CMP end-point.

FIGS. 3A-3B illustrate another example of conducting analysis of captured CMP products for CMP end-point detection. FIGS. 3A-3B include graphs 210A and 210B that are energy spectrum versus intensity plots, similar to graphs 200A and 200B shown in FIGS. 2A-2B. In other words, the graphs 210A and 210B also each have a Y-axis that represents intensity, and an X-axis that represents energy spectrum. The graph 210A corresponds to a first point in time, for example at or near a beginning of the CMP process. The graph 210B corresponds to a second point in time, for example at or near an end of the CMP process.

Whereas FIGS. 2A-2B are associated with the CMP of a tungsten plug, FIGS. 3A-3B are associated with the CMP of copper, for example a copper metal line in a multilayer interconnect structure. Thus, the elements to be detected in the captured CMP byproduct samples include Cu, Ta, and Si. As shown in FIG. 3B, the element silicon (Si) may have a corresponding energy band of between about 1.5 KeV and about 2.1 KeV, the element copper (Cu) may have a corresponding energy band of between about 7.8 KeV and about 8.2 KeV, and the element tantalum (Ta) may have a corresponding energy band of between about 8.2 KeV and about 8.6 KeV.

Since the graph 210A is associated with the beginning of the CMP process, the presence of the elements Cu, Ta, and Si is low in the graph 210A, which is demonstrated by the low (almost non-existent) peaks of the energy bands associated with Cu, Ta, and Si. This is attributed to the fact that not much of the wafer has been polished yet. Since FIG. 3B corresponds to a point in time at or near an end of the CMP process, where a sufficient amount of the wafer has been polished off, the peaks of the elements Cu, Ta, and Si are high in the graph 210B in FIG. 3B. Again, for the CMP process control to determine that the CMP end-point has been reached, the peaks of the elements Cu, Ta, and Si need to meet their respective intensity thresholds as well. For example, the peak of the element Cu needs to reach the intensity threshold 215. The other elements Ta and Si may have different intensity thresholds too. Once the peaks of the elements Cu, Ta, and Si have been reached, the CMP process control may instruct the CMP tool 110 to end the CMP process.

It is understood that the tungsten plug CMP and metal line CMP processes associated with FIGS. 2A-2B and 3A-3B are merely non-limiting examples of CMP processes. The same concept may apply to other CMP processes such as oxide CMP, wafer reclaim polish, aluminum CMP, other metal CMP, polysilicon CMP, etc.

The present disclosure may also detect and analyze a chronological sequence in which the various elements appear at different points in time of the CMP process. The CMP process control may evaluate the CMP process and perform process controls based on the detected sequence. As a first example of such sequence, FIGS. 4A, 4B, 4C and 4D illustrate respective energy spectrum versus intensity graphs 300A, 300B, 300C, and 300D that each correspond to a different point in time of the CMP process. Similar to FIGS. 2A-2B, the CMP process in FIGS. 4A-4D is the tungsten plug CMP process.

Figure 4A:
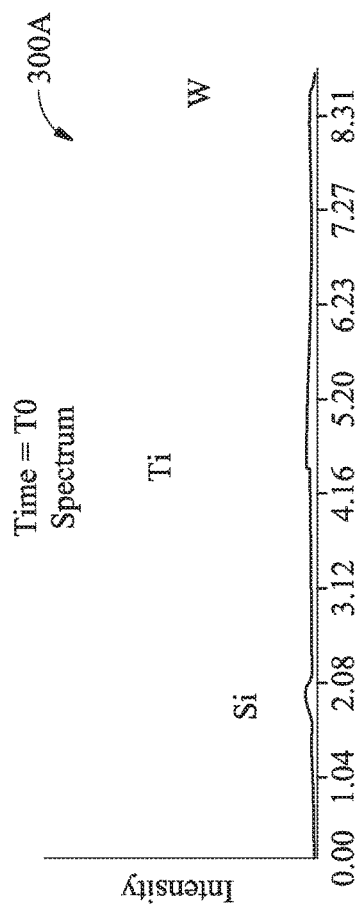
Figure 4B:
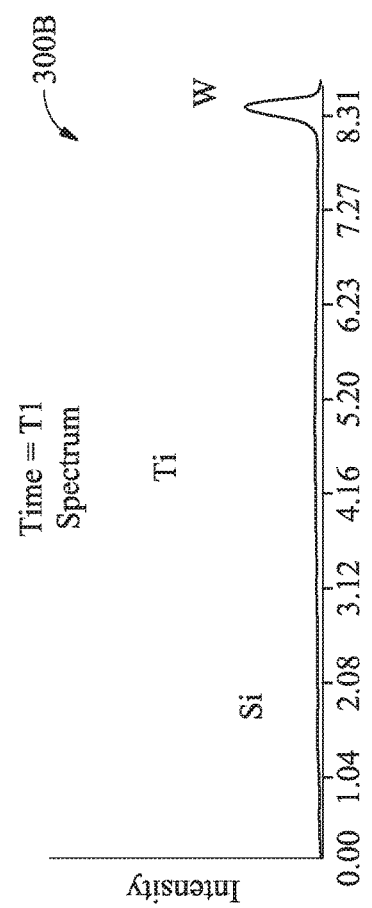
Figure 4C:
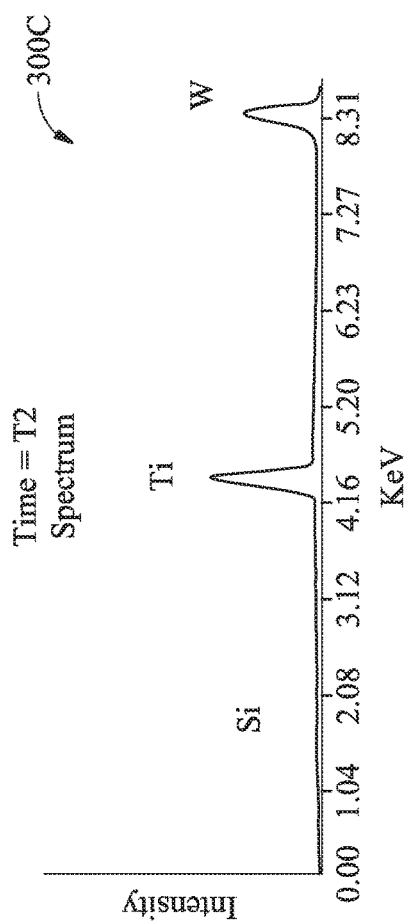
Figure 4D:
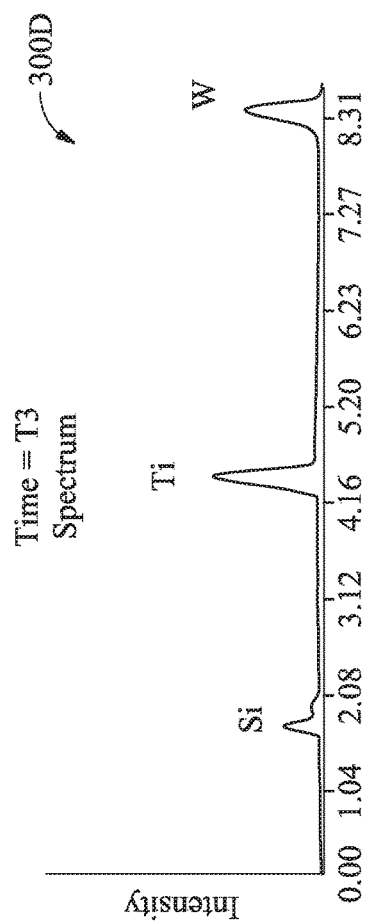
Figure 5C:
Figure 5D:
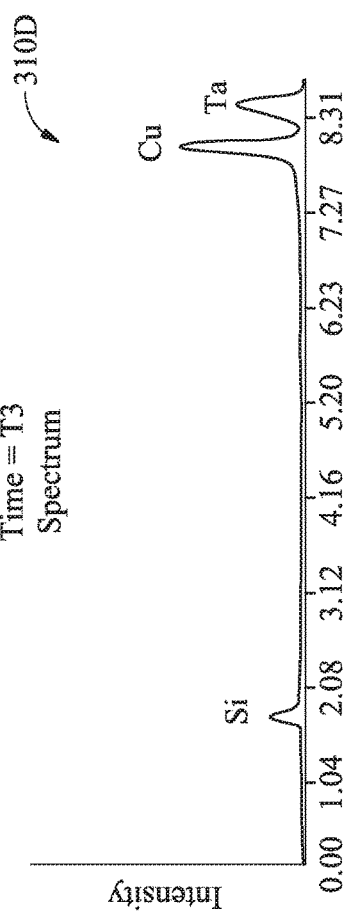

A time of T0 corresponds to a point in time at or near the beginning of the tungsten plug CMP process, which means not much of the wafer has been polished yet. This is shown in FIG. 4A, as the lack of wafer polishing is manifested by the low intensities of the elements Si, Ti, and W in the graph 300A.

A time of T1 occurs after T0. In some embodiments, a delta (time difference) between T0 and T1 is in a range from about 0.01 seconds to about 100 seconds. At the time T1, some of the wafer has been polished, as demonstrated by the presence of W in the graph 300B of FIG. 4B. The appearance of W before the other elements is attributed to the fact that the CMP process performed herein should reach the W first, before reaching the parts of the wafer that contain the other elements.

A time of T2 occurs after T1. In some embodiments, a delta (time difference) between T2 and T1 is in a range from about 1 second to about 3 seconds. At the time T2, even more of the wafer has been polished, as demonstrated by the presence of not only W, but also Ti, in the graph 300C of FIG. 4C. The appearance of Ti after W is also expected if the CMP process is performed correctly, since the part of the wafer that contain Ti is below the uppermost portions of the W material. Therefore, a correctly-performed CMP process should polish off some W first, and then polish off some materials that contain Ti. The delta between T1 and T2 is configured sufficiently long herein so that Ti is expected to appear at T2.

A time of T3 occurs after T2. In some embodiments, a delta (time difference) between T3 and T2 is in a range from about 1 second to about 3 seconds. At the time T3, the CMP process may be near its completion. As such, Si (in addition to Ti and W) is also expected to be visible in the graph 300D of FIG. 4D. The appearance of Si after W and Ti is also expected if the CMP process is performed correctly, since the part of the wafer that contain Si is further below the parts of the wafer that contain Ti and W. Therefore, a correctly-performed CMP process should polish off some W first, and then polish off some materials that contain Ti, and lastly polish off some materials that contain Si. The delta between T2 and T3 is configured sufficiently long herein so that Si is expected to appear at T3.

Again, the chronological sequence shown in the graphs 300A-300D of FIGS. 4A-4D demonstrate what should happen chronologically if the CMP process is performed correctly. However, if the CMP process is performed incorrectly, or if an unexpected problem occurs, the elements W, Ti, and Si may not appear in the chronological sequence depicted in FIGS. 4A-4D. If that (the incorrect chronological sequence) is observed, then the CMP process control system of the present disclosure may determine that an error may have occurred in the CMP process and may instruct the CMP tool to halt the CMP process, in order to investigate and correct the error.

As another example of the chronological sequence, FIGS. 5A, 5B, 5C and 5D illustrate respective energy spectrum versus intensity graphs 310A, 310B, 310C, and 310D that each correspond to a different point in time of the CMP process. Similar to FIGS. 3A-3B, the CMP process in FIGS. 5A-5D is the copper metal line CMP process.

A time of T0 corresponds to a point in time at or near the beginning of the copper metal line CMP process, which means not much of the wafer has been polished yet. This is shown in FIG. 5A, as the lack of wafer polishing is manifested by the low intensities of the elements Si, Cu, and Ta in the graph 310A.

A time of T1 occurs after T0. In some embodiments, a delta (time difference) between T0 and T1 is in a range from about 0.01 seconds to about 100 seconds. At the time T1, some of the wafer has been polished, as demonstrated by the presence of Cu in the graph 310B of FIG. 5B. The appearance of Cu before the other elements is attributed to the fact that the CMP process performed herein should reach the copper first, before reaching the parts of the wafer that contain the other elements.

A time of T2 occurs after T1. In some embodiments, a delta (time difference) between T2 and T1 is in a range from about 1 second to about 3 seconds. At the time T2, even more of the wafer has been polished, as demonstrated by the presence of not only Cu, but also Ta, in the graph 310C of FIG. 5C. The appearance of Ta after Cu is also expected if the CMP process is performed correctly, since the part of the wafer that contain Ta is below the uppermost portions of the Cu material. Therefore, a correctly-performed CMP process should polish off some Cu first, and then polish off some materials that contain Ta. The delta between T1 and T2 is configured sufficiently long herein so that Ta is expected to appear at T2.

A time of T3 occurs after T2. In some embodiments, a delta (time difference) between T3 and T2 is in a range from about 1 second to about 3 seconds. At the time T3, the CMP process may be near its completion. As such, Si (in addition to Cu and Ta) is also expected to be visible in the graph 310D of FIG. 5D. The appearance of Si after Cu and Ta is also expected if the CMP process is performed correctly, since the part of the wafer that contain Si is further below the parts of the wafer that contain Cu and Ta. Therefore, a correctly-performed CMP process should polish off some Cu first, and then polish off some materials that contain Ta, and lastly polish off some materials that contain Si. The delta between T2 and T3 is configured sufficiently long herein so that Si is expected to appear at T3.

Again, the chronological sequence shown in the graphs 310A-310D of FIGS. 5A-5D demonstrate what should happen chronologically if the CMP process is performed correctly. However, if the CMP process is performed incorrectly, or if an unexpected problem occurs, the elements Cu, Ta, and Si may not appear in the chronological sequence depicted in FIGS. 5A-5D. If that (the incorrect chronological sequence) is observed, then the CMP process control system of the present disclosure will know something is wrong and may instruct the CMP tool to halt the CMP process.

Figure 6A:
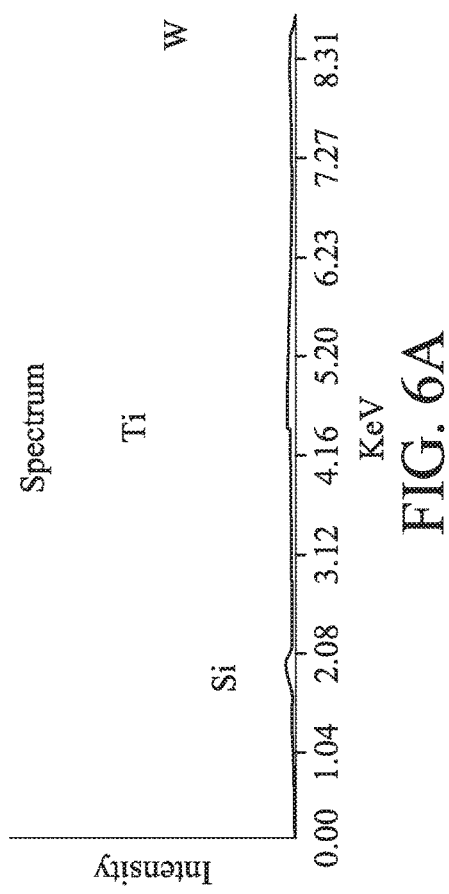
Figure 6B:
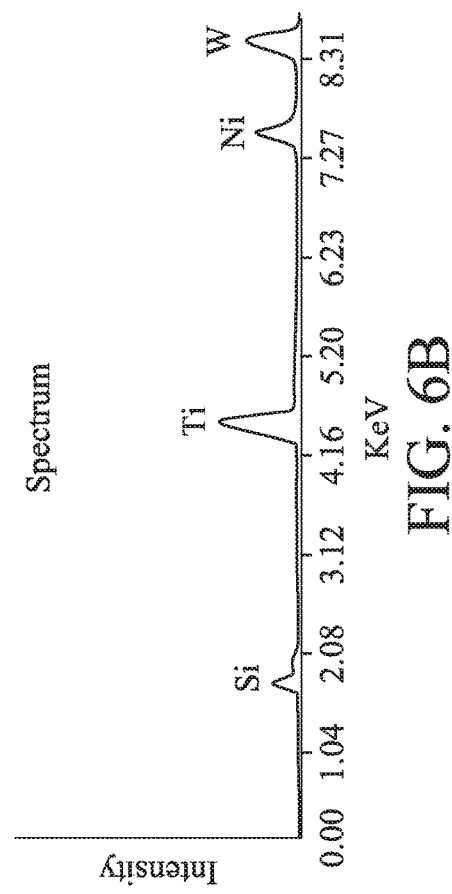
Figure 7A:
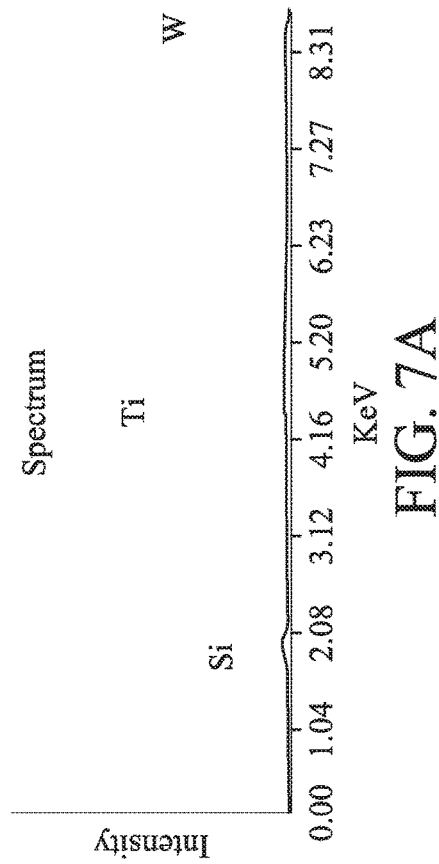
Figure 7B:
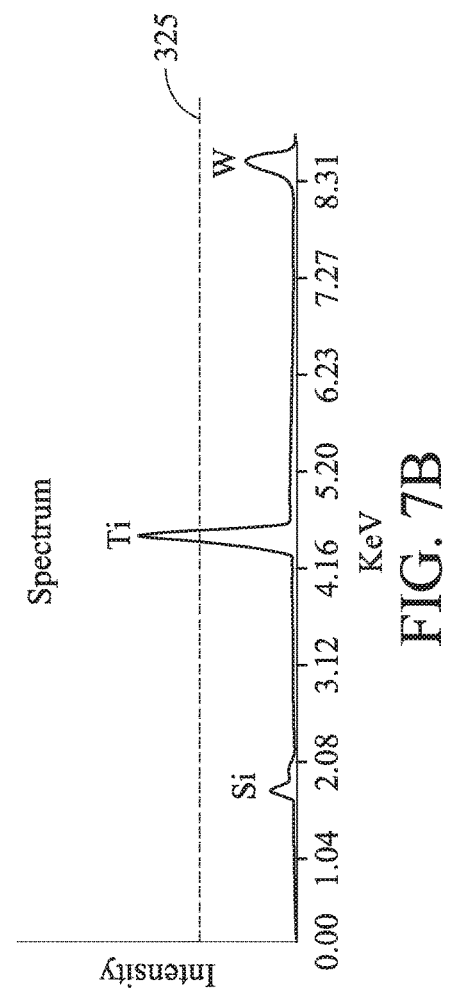
Figure 8A:
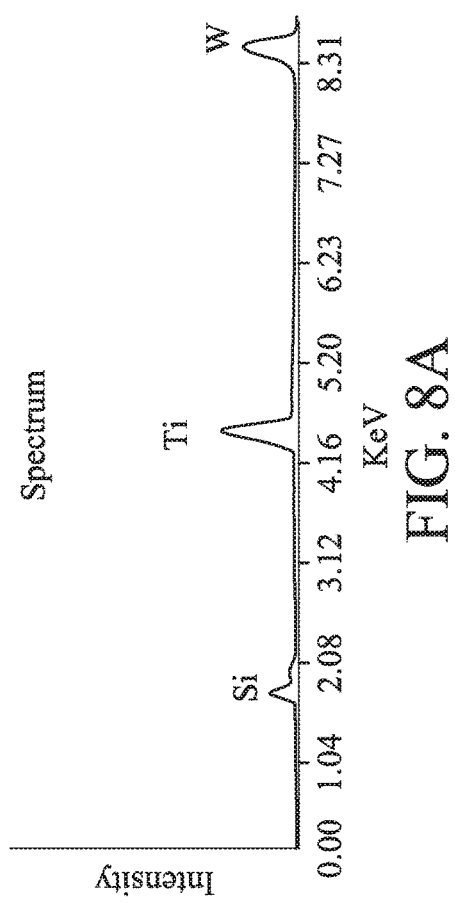
Figure 8B:
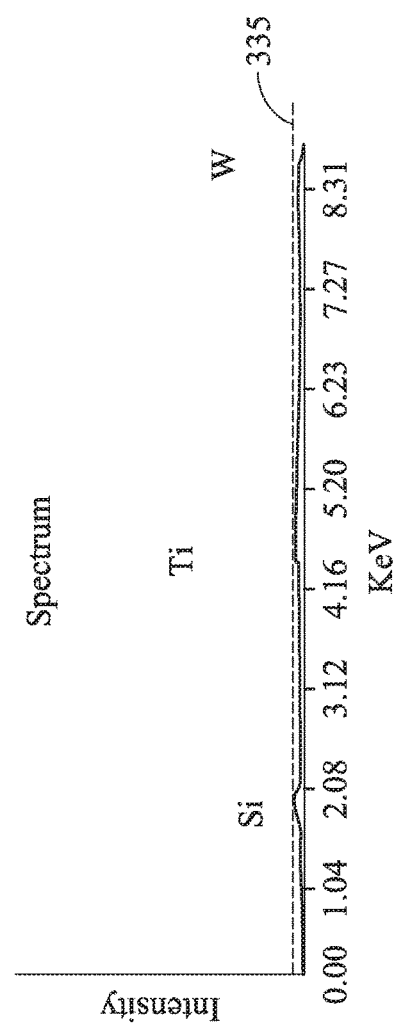

Some additional examples of using analysis of the CMP byproduct samples to perform CMP process control are illustrated in FIGS. 6A-6B, 7A-7B, and 8A-8B. FIGS. 6A, 7A, 8A are energy spectrum versus intensity plots at a second point in time, and FIGS. 6B, 7B, 8B are energy spectrum versus intensity plots at a first point in time. One aspect of the CMP process controls involves error detection. As an example, a presence of an unexpected element in the captured CMP byproduct samples may indicate that an error may have occurred in the CMP process. This is illustrated in FIGS. 6A-6B, which may be associated with the tungsten plug CMP discussed above as an example. In FIG. 6A, the CMP process has just begun, and thus the presence of the elements W, Ti, and Si is low in the captured CMP byproduct samples, as represented by the low intensities associated with these elements.

In FIG. 6B, which occurs at some time after (e.g., 20 seconds to 40 seconds after) the time associated with FIG. 6A, the CMP process has been performed sufficiently long so that the presence of the elements W, Ti, and Si is clearly visible in the graph. However, the presence of an extra and unexpected element nickel (Ni) is also detected via the analysis of the captured CMP byproduct sample, as indicated by a clearly visible peak at the energy band corresponding to Ni (e.g., between about 7.2 KeV and about 7.6 KeV). The unexpected presence of Ni means that there is a problem with the CMP process. For example, contaminant materials (e.g., materials containing Ni) may have been inadvertently introduced in the CMP tool. In some embodiments, the peak of the extra or unexpected element (e.g., Ni in this case) needs to meet or exceed an intensity threshold in order for the CMP process control system to determine that a problem or error exists (e.g., contaminants in the CMP tool). In any case, once the CMP process control system determines that a problem or error does exist (based on the detected presence of the unexpected element), the CMP process control system may instruct the CMP tool to stop, so that the problem or error may be investigated and corrected before further CMP processing can resume. It is understood that Ni is used herein merely as a non-limiting example of the unexpected element. In other embodiments, additional elements may be detected that could indicate a problem with the CMP process.

As another example, a problem of the CMP process may also be detected if any of the expected elements have an intensity peak that is too high. This is shown in FIGS. 7A-7B, which as an example may also be associated with the tungsten plug CMP discussed above. In FIG. 7A, the CMP process has just begun, and thus the presence of the elements W, Ti, and Si is low in the captured CMP byproduct samples, as represented by the low intensities associated with these elements.

In FIG. 7B, which occurs at some time after (e.g., 20 seconds to 40 seconds after) the time associated with FIG. 7A, the CMP process has been performed sufficiently long so that the presence of the elements W, Ti, and Si is clearly visible in the graph. However, Ti has a peak intensity that significantly exceeds an expected intensity threshold 325 for Ti. For example, the peak intensity of Ti is about 1.5 times the expected intensity threshold 325. In some embodiments, the presence of an element may be deemed too much if the peak intensity of that element exceeds the expected intensity threshold by at least 10%, for example by more than about 25%, by more than about 50%, or by more than about 100%.

The fact that the peak intensity of Ti significantly exceeds the expected intensity threshold 325 may mean that there is too much Ti in the captured CMP byproduct sample, which could indicate a problem or error with the CMP process. Accordingly, the CMP process control system may instruct the CMP tool to stop, so that the problem or error may be investigated and corrected before further CMP processing can resume. It is understood that the peak of Ti is used herein merely as a non-limiting example of an element having a stronger-than-expected peak. In other embodiments, stronger-than-expected peaks may be detected for other elements, which could also indicate a problem with the CMP process.

As yet another example, an analysis of the captured CMP byproduct samples may be used to determine when a cleaning process can be stopped. This is shown in FIGS. 8A-B. In FIG. 8A, a CMP process—such as the tungsten plug CMP process discussed above—has been performed for some time. As discussed above, the CMP process may include polishing steps (e.g., performed by the polishing unit of the CMP tool 110 of FIG. 1) and cleaning steps (e.g., performed by the cleaner unit of the CMP tool 110). The captured CMP byproduct samples may include byproduct samples from either the polishing unit, or from the cleaner unit, or both. In the example shown in FIGS. 8A-8B, the captured byproduct CMP samples may be collected from the cleaner unit. At the point in time corresponding to FIG. 8A, the presence of the elements Ti, and Si is still high in the captured CMP byproduct samples, since FIG. 8A may represent close to a beginning of the cleaning process. In other words, not much cleaning has been done yet at the point in time associated with FIG. 8A, which explains why the peak intensities for the expected elements Ti, W, and Si are still relatively high.

In FIG. 8B, which occurs at some time after (e.g., 5 seconds to 20 seconds after) the time associated with FIG. 8A, the cleaning process has been performed sufficiently long so that much of the debris from the polishing step should be washed away by this point. As such, the presence of the elements W, Ti, and Si should be low, as shown in FIG. 8B. The low presence of the elements W, Ti, and Si may indicate that the cleaning process has been performed satisfactorily and can be finished. In some embodiments, all of the peak intensities of the elements W, Ti, and Si have to be below a peak intensity threshold 335 in order for the CMP process control system herein to determine that the amounts of the elements W, Ti, and Si are sufficiently low, so that the cleaning process can be finished. In this manner, the present disclosure can use the analysis of captured CMP byproduct samples to not only determine the endpoint for the polishing process, or catch irregularities in the polishing process, but also determine the endpoint for the cleaning process or catch irregularities in the cleaning process (for example by detecting unexpected elements in the byproducts captured at the cleaning stage).

Figure 9:
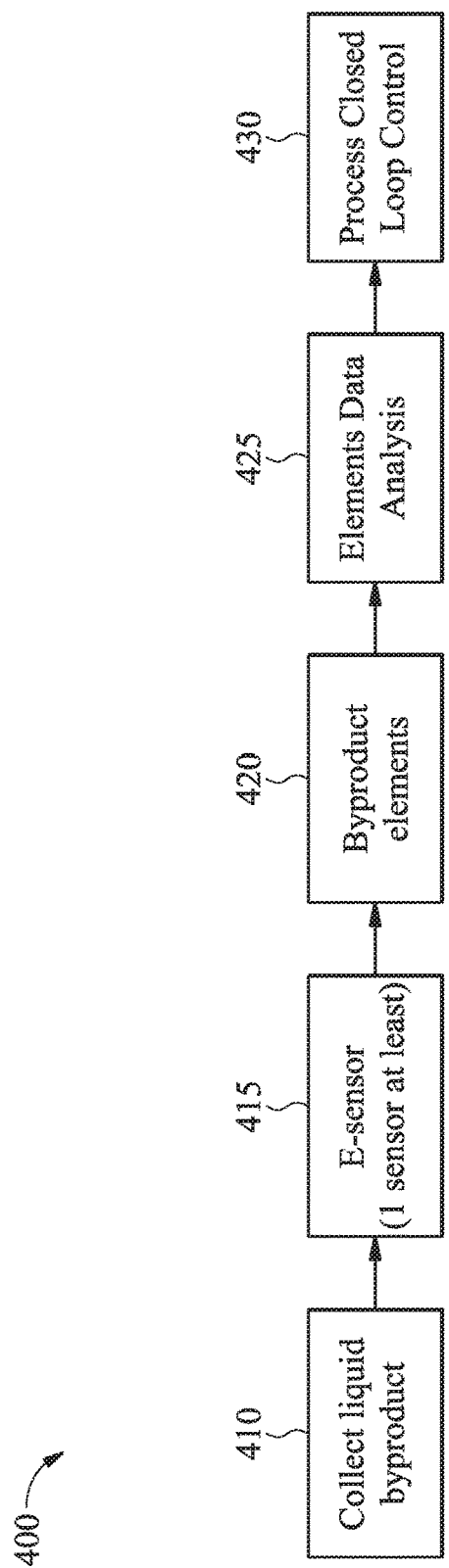
FIGS. 9-11 illustrate several process flows according to various embodiments of the present disclosure.
Figure 10:
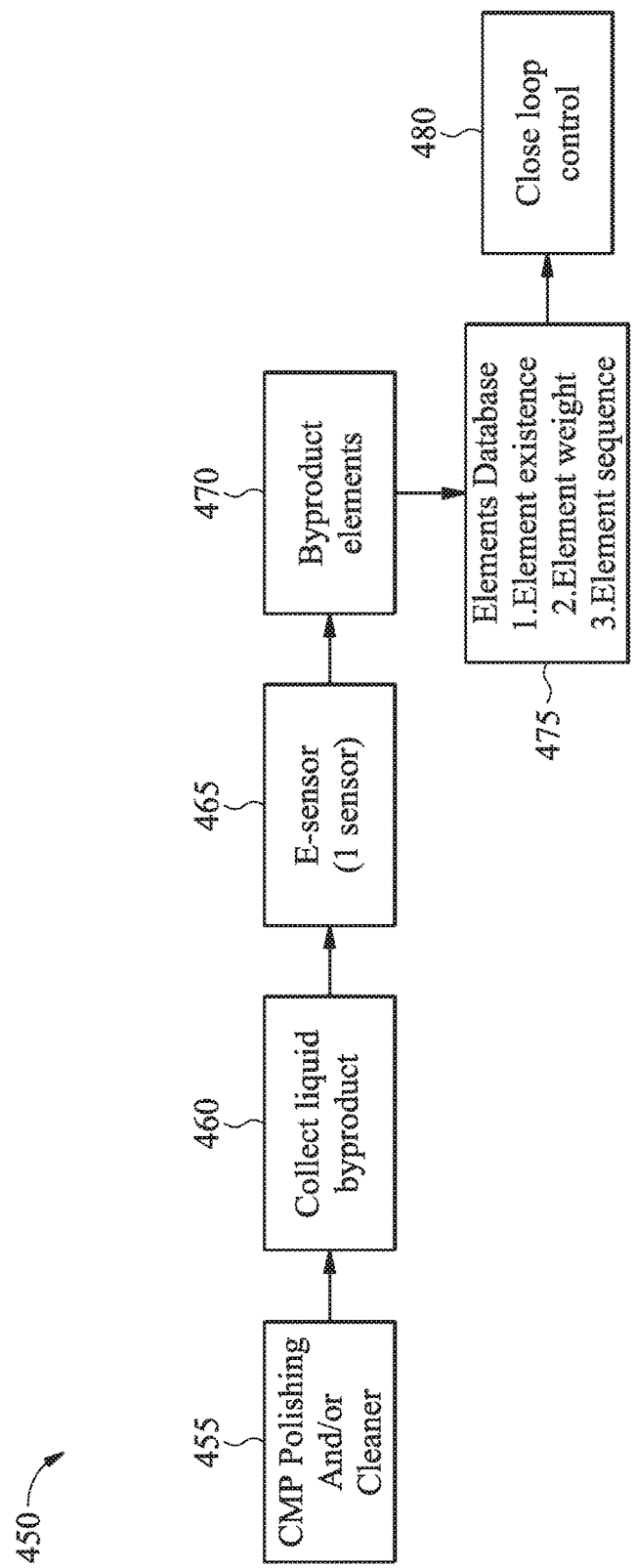
Figure 11:
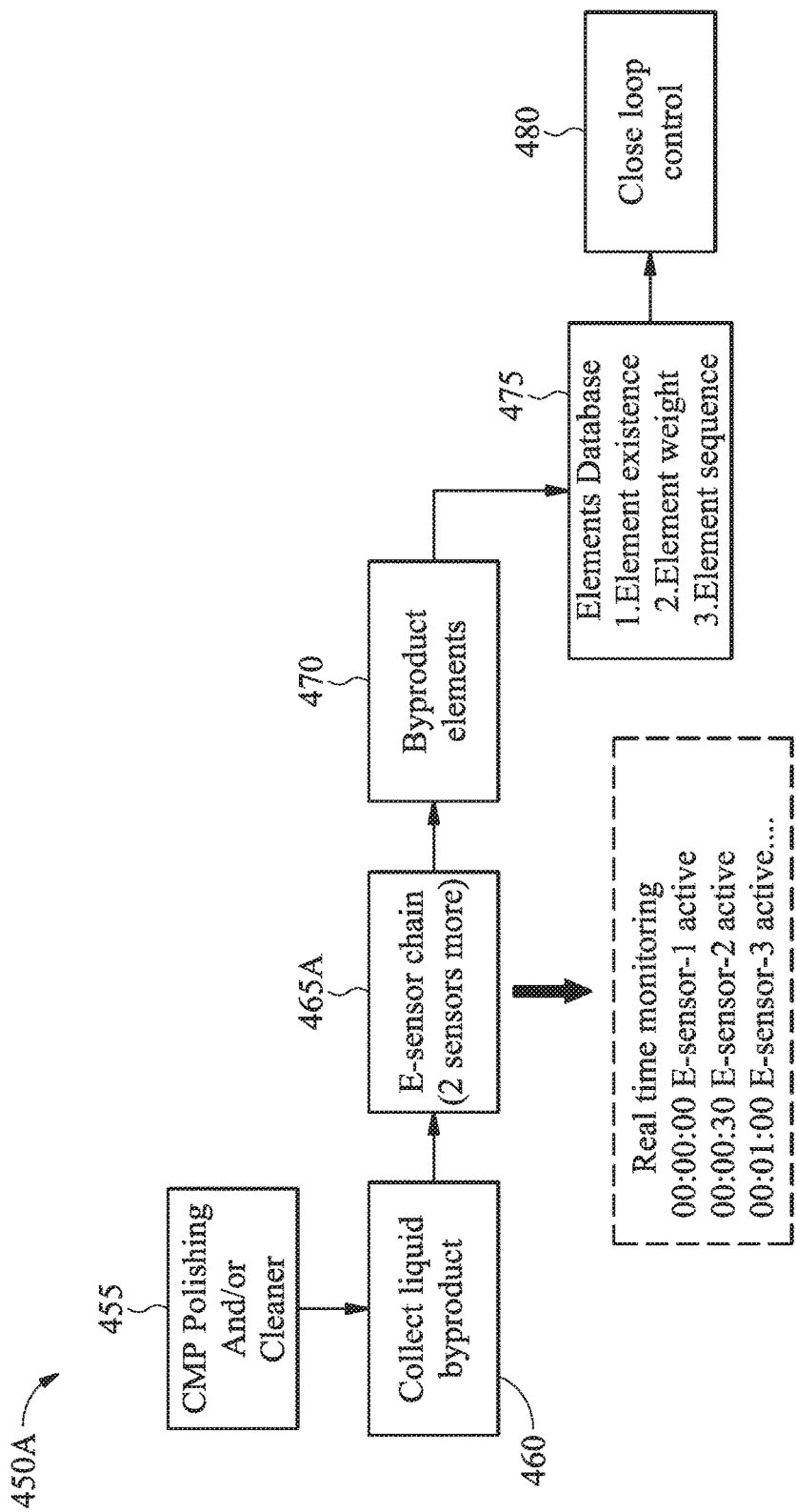

FIGS. 9-11 illustrate several simplified example process flows for CMP process control according to various embodiments of the present disclosure. For example, FIG. 9 illustrates a process flow 400 involving an e-sensor system. In some embodiments, the e-sensor system includes the e-sensor device 160 and the X-ray station (or another industrial-grade computer system) of FIG. 1. The process flow 400 includes a step 410 to collect liquid byproduct. The liquid byproduct may be collected from the polishing unit or the cleaner unit of the CMP tool and may include residue or debris associated with polishing the wafer or cleaning the wafer. The process flow 400 proceeds to a step 415 to analyze the captured byproduct using the e-sensor, for example by shooting a ray or a wave such as an X-ray at the captured byproduct. The process flow 400 proceeds to a step 420 to determine the presence and intensity of elements based on the e-sensor analysis of the captured byproduct. Different elements may be expected for different types of CMP processes. For example, the elements W, Ti, and Si may be expected for a tungsten plug CMP process. The process flow 400 proceeds to a step 425 to perform elements data analysis. As an example, the presence and/or intensity of the elements in the captured byproduct may be compared with wafer data in a database. As another example, the data from a subsequent wafer may be compared with the data from a previous wafer. Even within the same wafer, the data may be compared between different polishing/cleaning processes/steps, or from different polishing/cleaning chambers. The process flow 400 proceeds to a step 430 to perform closed loop process control based on the elements data analysis. For example, the elements data analysis results may be fed back to the CMP tools to adjust the CMP process.

FIG. 10 illustrates a process flow 450 involving a CMP process control system. The process flow 450 includes a step 455, in which a CMP tool is used to polish and/or clean a wafer. The process flow 450 also includes steps 460, 465, and 470 that are similar to the steps 410, 415, and 420, respectively, that are discussed above with reference to FIG. 9. For reasons of simplicity, the steps 460-470 are not discussed in detail herein (since they are similar to the steps 410-420). At a step 475, the process flow 450 analyzes an elements database to determine an existence of elements, the weighting (e.g., intensity) of the elements, and/or a chronological sequence in which the elements appear. At a step 480, closed loop CMP process control is performed. If the correct elements appear in the expected chronological sequence, and with the correct weighting, then the step 480 may be used to perform actions such as endpoint detection, or it may be used to instruct the CMP tool to further polish or clean the wafer. If an abnormality occurs, such as a detection of an unknown element in the captured byproduct sample, or if any element's weighting is too strong (e.g., the intensity peak is too high), then the step 480 may instruct the CMP tool to halt its processes, until the problems are investigated and corrected. It is understood that the process flow 450 is not limited to CMP processing of semiconductor wafers, but that it may apply in other situations or facilities, such as in the fabrication of LEDs, LCDs, wafer bumping, solar, etc. It is also applicable to a variety of technology nodes, including but not limited to N3, N5, N7, N10, N16, and N20, etc.

FIG. 11 illustrates a process flow 450A that is a slight modification of the process flow 450 discussed above in association with FIG. 10. Instead of using an e-sensor 465, the process flow 450A uses an e-sensor chain 465A, where two or more e-sensors (and optionally multiple byproduct capture tools) are used. The use of multiple e-sensors allows for almost real-time monitoring. For example, at time 00:00:00, e-sensor-1may be active. At time 00:00:30 (i.e., 30 seconds later), e-sensor-2 may be active. At time 00:01:00 (i.e., another 30 seconds later, or 1 minute from when e-sensor 1 was active), e-sensor-3 is active. Of course, the 30 seconds of time delta between the various e-sensors herein is merely a non-limiting example, and other embodiments may use different time deltas. In some embodiments, a subset of the e-sensors may be used for the polishing steps, while another subset of the e-sensors may be used for the cleaning steps. The multiple e-sensors may also correspond to the same wafer, or correspond to different wafers. Regardless of how the e-sensor chain is configured, more data sets may be collected, and the data may be used to provide almost real-time-like feedback to the CMP tool to adjust its processes, or to halt its processes, depending on the situation.

Figure 12:
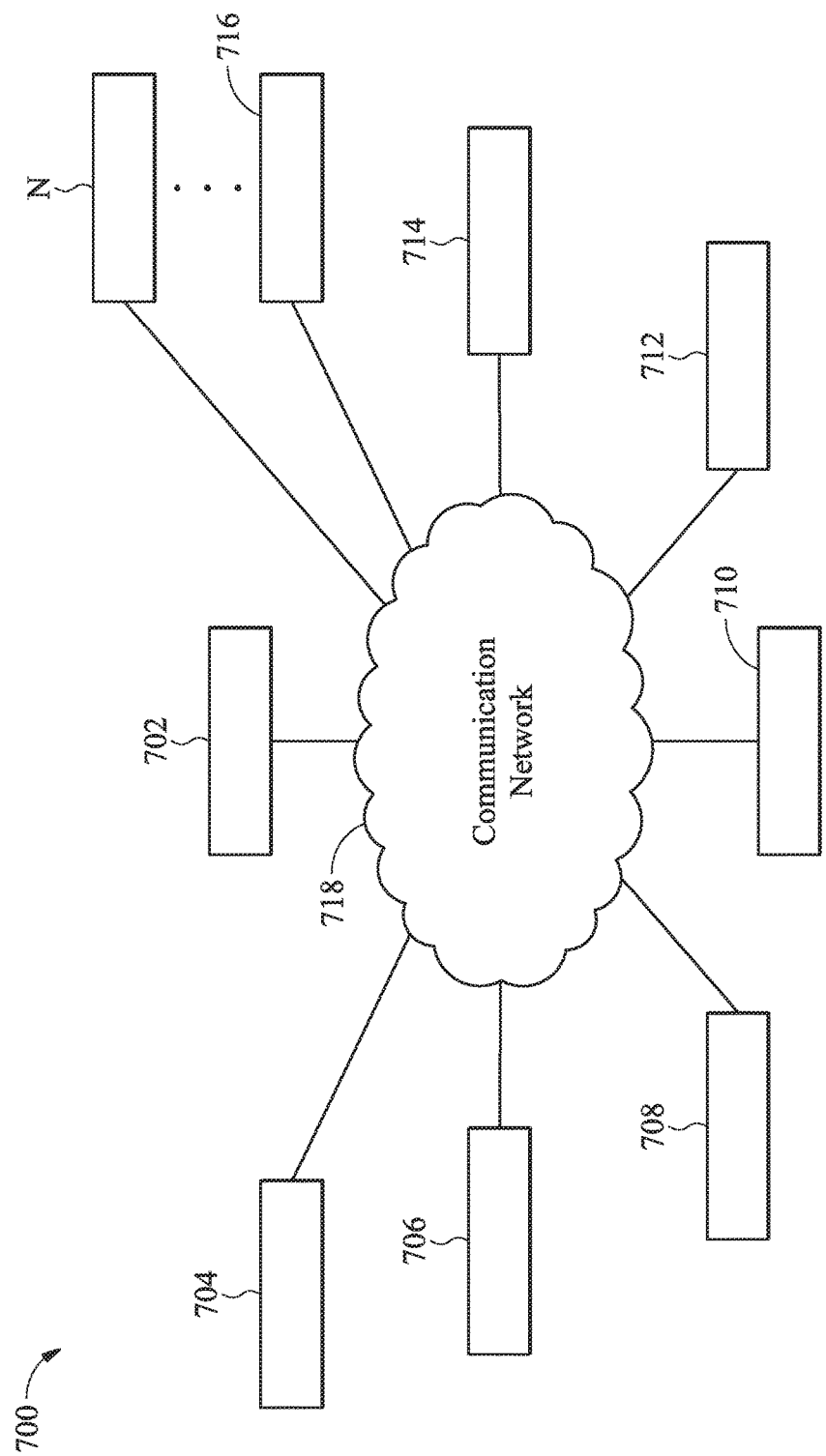
FIG. 12 illustrates an integrated circuit fabrication system according to various embodiments of the present disclosure.

FIG. 12 illustrates an integrated circuit fabrication system 700 according to embodiments of the present disclosure. The fabrication system 700 includes a plurality of entities 702, 704, 706, 708, 710, 712, 714, 716 . . . , N that are connected by a communications network 718. The network 718 may be a single network or may be a variety of different networks, such as an intranet and the Internet, and may include both wire line and wireless communication channels.

In an embodiment, the entity 702 represents a service system for manufacturing collaboration; the entity 704 represents an user, such as product engineer monitoring the interested products; the entity 706 represents an engineer, such as a processing engineer to control process and the relevant recipes, or an equipment engineer to monitor or tune the conditions and setting of the processing tools; the entity 708 represents a metrology tool for IC testing and measurement; the entity 710 represents a semiconductor processing tool, such as any of the tools of the CMP processing control system 100 discussed above with reference to FIG. 1; the entity 712 represents a virtual metrology module associated with the processing tool 710; the entity 714 represents an advanced processing control module associated with the processing tool 710 and additionally other processing tools; and the entity 716 represents a sampling module associated with the processing tool 710.

Each entity may interact with other entities and may provide integrated circuit fabrication, processing control, and/or calculating capability to and/or receive such capabilities from the other entities. Each entity may also include one or more computer systems for performing calculations and carrying out automations. For example, the advanced processing control module of the entity 714 may include a plurality of computer hardware having software instructions encoded therein. The computer hardware may include hard drives, flash drives, CD-ROMs, RAM memory, display devices (e.g., monitors), input/output device (e.g., mouse and keyboard). The software instructions may be written in any suitable programming language and may be designed to carry out specific tasks, such as the tasks associated with optimizing the CMP process controls as discussed above.

The integrated circuit fabrication system 700 enables interaction among the entities for the purpose of integrated circuit (IC) manufacturing, as well as the advanced processing control of the IC manufacturing. In an embodiment, the advanced processing control includes adjusting the processing conditions, settings, and/or recipes of one processing tool applicable to the relevant wafers according to the metrology results.

In another embodiment, the metrology results are measured from a subset of processed wafers according to an optimal sampling rate determined based on the process quality and/or product quality. In yet another embodiment, the metrology results are measured from chosen fields and points of the subset of processed wafers according to an optimal sampling field/point determined based on various characteristics of the process quality and/or product quality.

One of the capabilities provided by the IC fabrication system 700 may enable collaboration and information access in such areas as design, engineering, and processing, metrology, and advanced processing control. Another capability provided by the IC fabrication system 700 may integrate systems between facilities, such as between the metrology tool and the processing tool. Such integration enables facilities to coordinate their activities. For example, integrating the metrology tool and the processing tool may enable manufacturing information to be incorporated more efficiently into the fabrication process or the APC module, and may enable wafer data from the online or in site measurement with the metrology tool integrated in the associated processing tool.

Figure 13:
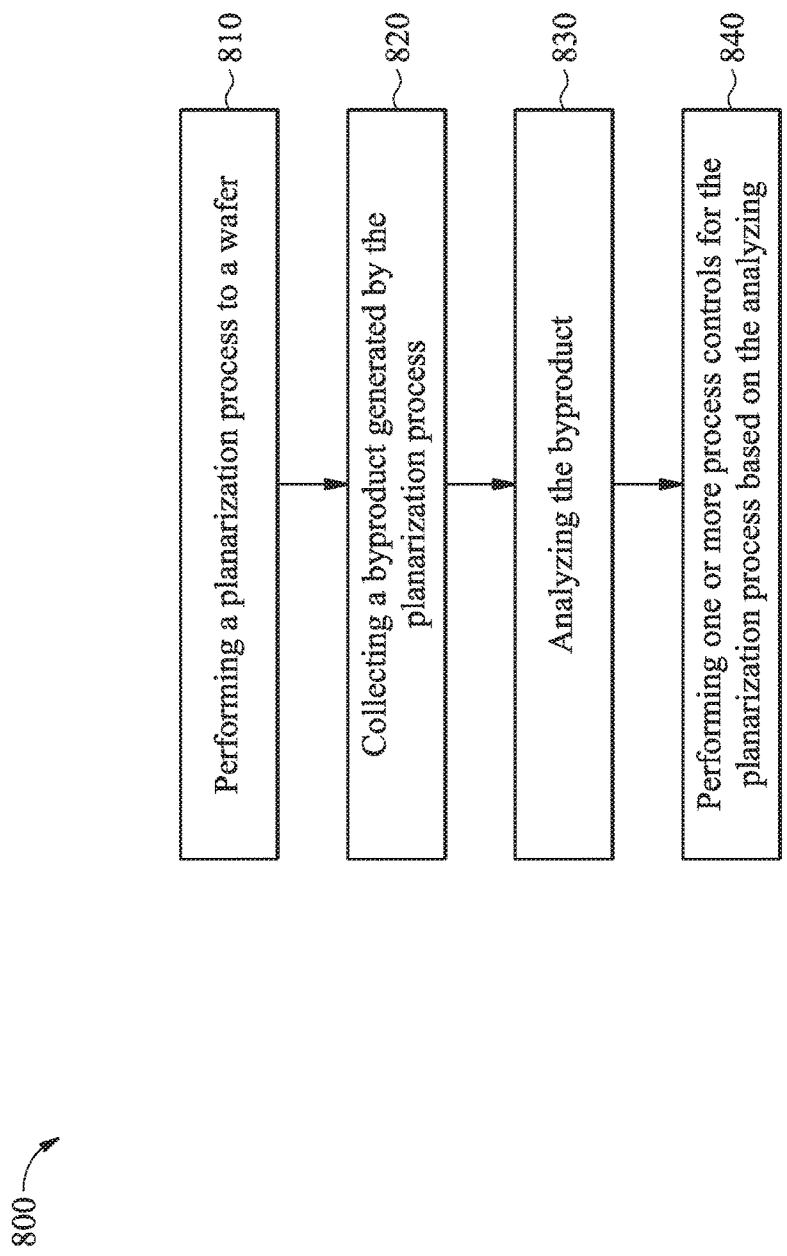
FIGS. 13-14 are flowcharts illustrating example methods of performing planarization process controls according to embodiments of the present disclosure.

FIG. 13 is a flowchart illustrating a method 800 of performing planarization process control according to embodiments of the present disclosure. The method 800 includes a step 810 of performing a planarization process to a wafer. In some embodiments, the step 810 includes performing a chemical mechanical polishing (CMP) process.

The method 800 includes a step 820 of collecting a byproduct generated by the planarization process. In some embodiments, the step 820 includes collecting a liquid that contains the byproduct from a planarization tool that is used to perform the planarization process.

The method 800 includes a step 830 of analyzing the byproduct. In some embodiments, the step 830 includes applying a ray or a wave to the byproduct. In some embodiments, the ray or the wave includes an X-ray. In some embodiments, the analyzing is performed using a plurality of e-sensor devices. In some embodiments, the plurality of e-sensor devices are configured to collect the byproduct at different points in time or from different parts of a planarization tool used to perform the planarization process. In some embodiments, the analyzing comprises identifying one or more elements included in the byproduct.

The method 800 includes a step 840 of performing one or more process controls for the planarization process based on the analyzing. In some embodiments, the step 840 includes determining, based on the identifying of the one or more elements included in the byproduct, that an end-point for the planarization process has been reached. In some embodiments, the step 840 includes determining, based on the identifying of the one or more elements included in the byproduct, that the planarization process has an abnormality. In some embodiments, the step 840 includes determining that the planarization process has an abnormality in response to an identification of an unexpected element in the byproduct. In some embodiments, the step 840 includes determining that the planarization process has an abnormality in response to a greater-than-expected presence of the one or more elements in the byproduct. In some embodiments, the one or more elements include a plurality of elements, and wherein the step 840 includes determining that the planarization process has an abnormality in response to the plurality of elements in the byproduct being identified in an unexpected chronological sequence.

It is understood that additional steps may be performed, before, during, or after the steps 810-840 to complete the method 800. For reasons of simplicity, these additional steps are not discussed herein in detail.

Figure 14:
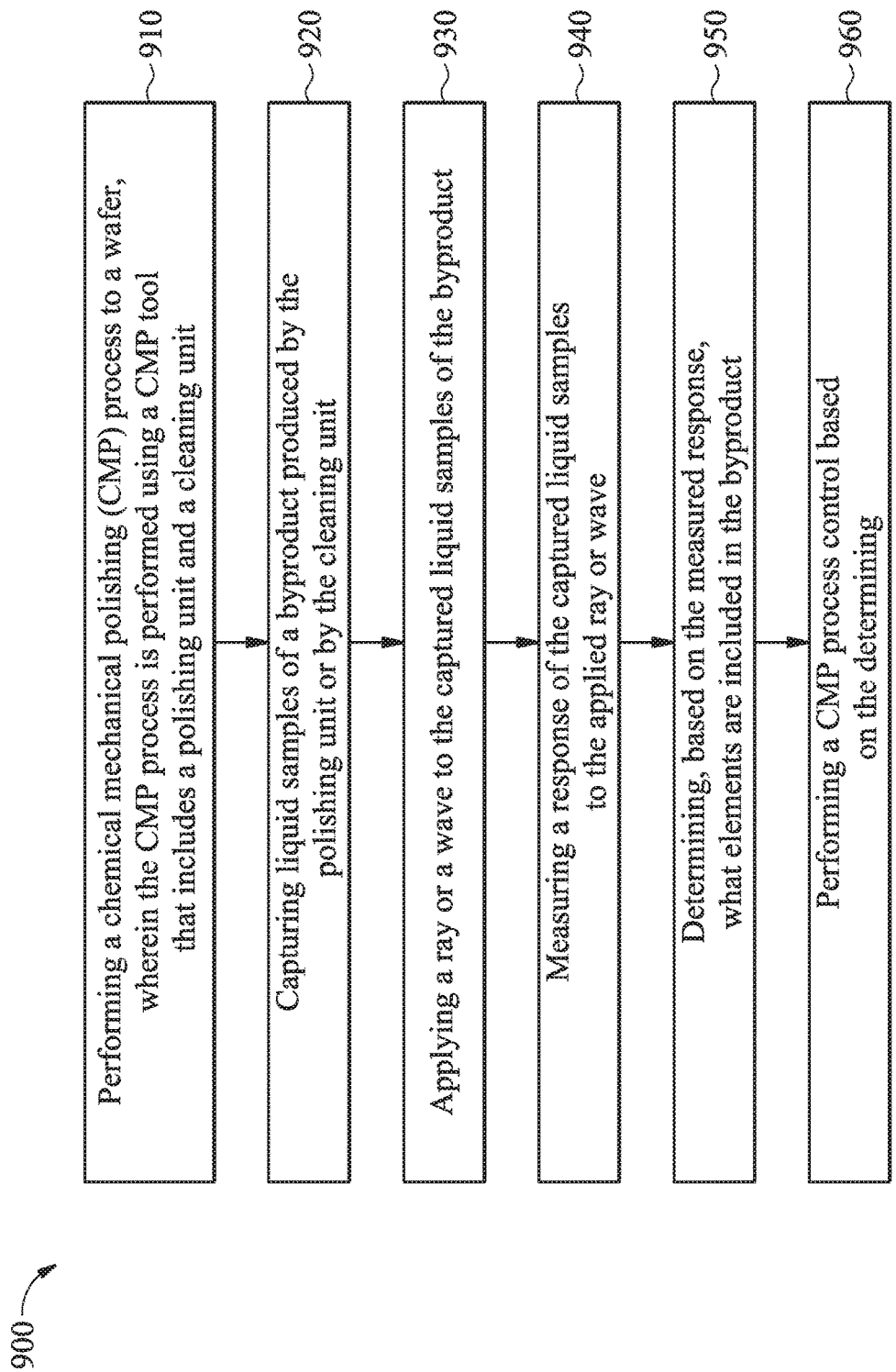

FIG. 14 is a flowchart illustrating a method 900 of performing planarization process control according to embodiments of the present disclosure. The method 900 includes a step 910 of performing a chemical mechanical polishing (CMP) process to a wafer. The CMP process is performed using a CMP tool that includes a polishing unit and a cleaning unit.

The method 900 includes a step 920 of capturing liquid samples of a byproduct produced by the polishing unit or by the cleaning unit.

The method 900 includes a step 930 of applying a ray or a wave to the captured liquid samples that contain the byproduct.

The method 900 includes a step 940 of measuring a response of the captured liquid samples to the applied ray or wave.

The method 900 includes a step 950 of determining, based on the measured response, what elements are included in the byproduct.

The method 900 includes a step 960 of performing a CMP process control based on the determining. In some embodiments, the performing the CMP process control comprises: determining an end-point for a polishing process performed by the polishing unit or for a cleaning process performed by the cleaning unit. In some embodiments, the performing the CMP process control comprises: halting the CMP process in response to a determination that an error has occurred.

It is understood that additional steps may be performed, before, during, or after the steps 910-960 to complete the method 900. For reasons of simplicity, these additional steps are not discussed herein in detail.

The present disclosure offers advantages over conventional methods of performing planarization processing control. It is understood, however, that other embodiments may offer additional advantages, and not all advantages are necessarily disclosed herein, and that no particular advantage is required for all embodiments. Conventional planarization methods such as CMP may rely on parameters such as polishing time or polishing rate for endpoint detection. However, these endpoint detection methods are not sufficiently accurate, and as a result the wafer may be over-polished or under-polished (or over-cleaned or under-cleaned). In comparison, the CMP processing controls of the present disclosure collect and analyze CMP byproduct samples and perform end-point detection based on the CMP byproduct analysis. This allows for more accurate end-point detections for both the polishing and cleaning processes associated with CMP. In addition, the CMP byproduct analysis may also reveal errors or problems with the CMP process, for example by detecting the presence of unknown elements in the CMP byproduct, or a stronger-than-expected presence of an element (even if that element itself is expected) in the CMP byproduct, or an unexpected chronological order in which expected elements appear in the CMP byproduct. As such, problems can be corrected promptly and will not significantly impact yield or device performance negatively. The processes and systems of the present disclosure are also compatible with existing process flow and thus are not costly to implement.

One aspect of the present disclosure involves a method. A planarization process is performed to a wafer. A byproduct generated by the planarization process is collected. The byproduct is analyzed. One or more process controls are performed for the planarization process based on the analyzing.

Another aspect of the present disclosure involves a method. A chemical mechanical polishing (CMP) process is performed to a wafer. The CMP process is performed using a CMP tool that includes a polishing unit and a cleaning unit. Liquid samples are captured. The liquid samples are of a byproduct produced by the polishing unit or by the cleaning unit. A ray or a wave is applied to the captured liquid samples of the byproduct. A response of the captured liquid samples to the applied ray or wave is measured. A determination is made, based on the measured response, what elements are included in the byproduct. A CMP process control is performed based on the determining.

Yet another aspect of the present disclosure involves system. The system includes planarization tool configured to perform a planarization process to a wafer. The system includes a byproduct-capture tool configured to capture samples of a byproduct generated as a part of the planarization process. The system includes an e-sensor tool configured to analyze a content of the samples of the byproduct captured by the byproduct-capture tool. The system includes one or more computers configured to perform one or more process controls for the planarization process based on an analysis produced by the e-sensor tool regarding the content of the captured samples.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The invention claimed is:

1. A method, comprising:
   performing a planarization process to a wafer, wherein the planarization process is performed using at least a polishing tool and a cleaning tool;
   collecting a first byproduct generated by the polishing tool and collecting a second byproduct generated by the cleaning tool during the planarization process;
   analyzing the first byproduct and the second byproduct; and
   performing one or more process controls for the planarization process based on the analyzing.

2. The method of claim 1, wherein the performing the planarization process comprises performing a chemical mechanical polishing (CMP) process analyzing comprises:
   monitoring an energy spectrum that includes a plurality of first energy bands and a plurality of second energy bands located between the first energy bands, wherein the first energy bands correspond to a plurality of known materials involved in the planarization process, and wherein the second energy bands correspond to materials that are not expected to be involved in the planarization process;
   detecting, based on the monitoring, that an intensity of one of the second energy bands exceeds a predetermined threshold;
   determining, in response to the detecting, that an abnormality has occurred in the planarization process; and
   adjusting the one or more process controls after the determining.

3. The method of claim 1, wherein the collecting comprises collecting a polishing liquid that contains the first byproduct and collecting a cleaning liquid that contains the second byproduct.

4. The method of claim 1, wherein the analyzing comprises applying a ray or a wave to the first byproduct and the second byproduct.

5. The method of claim 4, wherein the applying the ray or the wave comprises applying an X-ray.

6. The method of claim 1, wherein the analyzing is performed using a plurality of e-sensor devices, wherein a first subset of the e-sensor devices are used to analyze the first byproduct, and wherein a second subset of the e-sensor devices are used to analyze the second byproduct.

7. The method of claim 6, wherein the plurality of e-sensor devices are configured to collect the first by product and the second byproduct at different points in time.

8. The method of claim 1, wherein the analyzing comprises identifying one or more elements included in the first byproduct or in the second byproduct.

9. The method of claim 8, wherein the performing the one or more process controls comprises determining, based on the identifying of the one or more elements included in the first byproduct or in the second byproduct, that an end-point for the planarization process has been reached.

10. The method of claim 8, wherein the performing the one or more process controls comprises determining, based on the identifying of the one or more elements included in the first byproduct or in the second byproduct, that the planarization process has an abnormality.

11. The method of claim 10, wherein the determining comprises determining that the planarization process has an abnormality in response to an identification of an unexpected element in the first byproduct or in the second byproduct.

12. The method of claim 10, wherein the determining comprises determining that the planarization process has an abnormality in response to a greater-than-expected presence of the one or more elements in the first byproduct or in the second byproduct.

13. The method of claim 10, wherein the one or more elements include a plurality of elements, and wherein the determining comprises determining that the planarization process has an abnormality in response to the plurality of elements in the first byproduct or in the second byproduct being identified in an unexpected chronological sequence.

14. A method, comprising:
   performing a chemical mechanical polishing (CMP) process to a wafer, wherein the CMP process is performed using a CMP tool that includes a polishing unit and a cleaning unit;
   capturing liquid samples of a first byproduct produced by the polishing unit and a second byproduct produced by the cleaning unit;
   applying a ray or a wave to the captured liquid samples of the first byproduct and the second byproduct;
   measuring a response of the captured liquid samples to the applied ray or wave;
   determining, based on the measured response, what elements are included in the first byproduct and in the second byproduct; and
   performing a CMP process control based on the determining.

15. The method of claim 14, wherein the performing the CMP process control comprises:
   determining an end-point for a polishing process performed by the polishing unit or for a cleaning process performed by the cleaning unit; or
   halting the CMP process in response to a determination that an error has occurred.

16. A method, comprising:
   collecting, from a wafer polishing tool, a first liquid that is produced as a result of a polishing process being performed on a wafer by the wafer polishing tool;
   collecting, from a wafer cleaning tool, a second liquid that is produced as a result of a cleaning process being performed on the wafer by the wafer cleaning tool;
   identifying one or more elements contained in the collected first liquid and in the collected second liquid;

determining, based on the identifying of the one or more elements, that an end-point for the polishing process has been reached or that the polishing process has an abnormality; and performing one or more process controls with respect to the polishing process in response to the determining.

17. The method of claim 16, wherein the identifying comprises applying a ray or a wave to the collected first liquid and the collected second liquid.

18. The method of claim 16, wherein the identifying comprises collecting, using a plurality of e-sensor devices, the first liquid and the second liquid at different points in time, wherein the first liquid is collected using a first subset of the e-sensor devices, and wherein the second liquid is collected using a second subset of the e-sensor devices.

19. The method of claim 16, wherein the determining that the polishing process has an abnormality is based on a content of at least one of the one or more elements exceeding a predefined threshold.

20. The method of claim 16, wherein:
the identifying comprises ascertaining a chronological order in which a plurality of elements of the one or more elements are detected; and
the determining that the polishing process has an abnormality is based on the chronological order.

* * * * *